(12) United States Patent
Huang

(10) Patent No.: US 10,590,371 B1
(45) Date of Patent: Mar. 17, 2020

(54) METHOD AND DEVICE FOR FERMENTATION BASED ON MICROBIAL ASEXUAL REPRODUCTION

(71) Applicant: Ying-Ling Huang, Taichung (TW)

(72) Inventor: Ying-Ling Huang, Taichung (TW)

( * ) Notice: Subject to any disclaimer, the term of this patent is extended or adjusted under 35 U.S.C. 154(b) by 0 days.

(21) Appl. No.: 16/173,283

(22) Filed: Oct. 29, 2018

(51) Int. Cl.
| | | |
|---|---|---|
| *C12M 1/02* | (2006.01) | |
| *C12M 1/20* | (2006.01) | |
| *C12M 1/06* | (2006.01) | |
| *C12N 1/20* | (2006.01) | |
| *C12M 1/42* | (2006.01) | |
| *C01B 33/12* | (2006.01) | |
| *C12M 1/08* | (2006.01) | |
| *C12N 3/00* | (2006.01) | |

(52) U.S. Cl.
CPC .............. *C12M 1/02* (2013.01); *C01B 33/12* (2013.01); *C12M 1/06* (2013.01); *C12M 35/04* (2013.01); *C12M 35/08* (2013.01); *C12N 1/20* (2013.01); *C12M 1/08* (2013.01); *C12N 3/00* (2013.01)

(58) Field of Classification Search
CPC . C12M 1/02; C12M 1/06; C12M 1/20; C12M 35/04; C12M 35/08
See application file for complete search history.

(56) References Cited

U.S. PATENT DOCUMENTS

| | | | | |
|---|---|---|---|---|
| 5,627,068 A | * | 5/1997 | Kujumdzieva | .......... A61K 8/99 435/119 |
| 2013/0115333 A1 | * | 5/2013 | Crosato | ................ C12G 1/0203 426/15 |

FOREIGN PATENT DOCUMENTS

CN          104694344        *    6/2015

* cited by examiner

*Primary Examiner* — Ruth A Davis
(74) *Attorney, Agent, or Firm* — Rosenberg, Klein & Lee

(57) ABSTRACT

The present invention relates to a method and a device for fermentation based on a microbial asexual reproduction. The method comprises the steps of adding plural silica sands, a medium and a microorganism into a tank; and stirring for separating a cluster of the microorganism by a shear force generated from the plural silica sands and returning the microorganism to a logarithmic growth phase without undergoing a spore phase to increase a fermentation rate of the microorganism. The device comprises a tank, a speed control motor disposed outside the tank, a stirring component connected to the speed control motor, a refluxing mechanism for high pressure air and water connected to the tank, a heating unit disposed in the tank and a pumping motor connected to the tank.

6 Claims, 4 Drawing Sheets

METHOD AND DEVICE FOR FERMENTATION BASED ON MICROBIAL ASEXUAL REPRODUCTION

BACKGROUND OF THE INVENTION

1. Field of the Invention

The present invention relates to a method and a device for fermentation based on microbial asexual reproduction in order to promote reproduction and fermentation of microorganisms.

2. Description of Related Art

Wines and fruit vinegar are usually prepared by microbial fermentation, e.g. solid-state fermentation and liquid-state fermentation. Solid-state fermentation is a biologic reaction process of incubating one kind or more kinds of microorganisms in a humid solid-phase matrix without free flowing water, and liquid-state fermentation is a biologic reaction process using a liquid medium as a continuous phase.

The production capacity of solid-state fermentation is limited because it needs a long incubating time. Therefore, solid-state fermentation is not suitable applied in mass production. Liquid-state fermentation has a shorter incubating time, and the product quality of liquid-state fermentation is easily managed, so liquid-state fermentation is relatively suitable for a high-efficiency production process.

Although the fermentation efficiency of liquid-state fermentation is higher than solid-state fermentation, a microorganism has to undergo plural life cycles comprising a spore phase, a logarithmic growth phase, a stationary phase and a death phase to complete a fermentation process during liquid-state fermentation, so the incubating time for liquid-state fermentation still cannot be reduced efficiently.

SUMMARY OF THE INVENTION

The present invention relates to a method and a device for fermentation based on microbial asexual reproduction, which can promote a fermentation rate of a microorganism and reduce production time of a fermented food.

The microbial asexual reproduction-based fermentation method comprises the steps of adding a mixing solution containing plural silica sands, a medium, a carbohydrate and a microorganism into a tank; heating and stirring the mixing solution to a temperature with a stirring speed in the tank for separating a cluster of the microorganism by a shear force generated from the plural silica sands and returning the microorganism to a logarithmic growth phase without undergoing a spore phase; draining the mixing solution from a bottom of the tank; and refluxing the mixing solution into the tank together with a high pressure air for atomizing and blending oxygen into the mixing solution to obtain a small molecule water having high level of oxygen and increase oxygen content which is beneficial for reproduction of an aerobic microorganism.

According to an embodiment of the microbial asexual reproduction-based fermentation method, a weight ratio of the plural silica sands, the medium and the carbohydrate is 1:3-5:3-24.

According to an embodiment of the microbial asexual reproduction-based fermentation method, the medium is made of a soy powder.

According to an embodiment of the microbial asexual reproduction-based fermentation method, the carbohydrate is sucrose.

According to an embodiment of the microbial asexual reproduction-based fermentation method, the temperature is 37° C.

According to an embodiment of the microbial asexual reproduction-based fermentation method, the stirring speed is 300 rpm.

The device for microbial asexual reproduction-based fermentation comprises a tank, a speed control motor, a stirring component, a refluxing mechanism for high pressure air and water, a heating unit and a pumping motor.

The tank has a compartment, a ventilation valve, a feeding hole, an upper discharging opening and a lower discharging opening. The compartment is disposed around a lower region of a wall of the tank, and is provided with a first inlet at an upper end and a first outlet at a bottom end for injecting a fluid into or draining a fluid out of the compartment respectively. The ventilation valve is disposed at a top surface of the tank for adjusting a pressure of the tank. The feeding hole is used for importing a raw material into the tank, the upper discharging opening is used for collecting a fermentation broth, and the lower discharging opening is used for exporting plural silica sands, a medium and a microorganism.

The speed control motor is disposed outside the tank and having a power output terminal.

The stirring component comprises a transmission shaft and plural blades. The transmission shaft is connected to the power output terminal of the speed control motor and the plural blades are disposed on the transmission shaft at an interval.

The refluxing mechanism for high pressure air and water comprises a Venturi tube and a refluxing tube. The Venturi tube has a first input for importing a high pressure air, a second input, and an output connected to an upper side of the tank. The refluxing tube has a second outlet connecting to the second input of the Venturi tube, and a second inlet connecting to a lower side of the tank. A mixing solution in the tank is drained from the tank and injected to the Venturi tube and re-injected into the tank by the Venturi tube.

The heating unit is disposed corresponding to the compartment for heating the solution in the compartment.

The pumping motor has a third inlet and a third outlet. The third inlet is connected to a lower side of the compartment for inflow of the fluid from the compartment, and the third outlet is connected to an upper side of the compartment for outflow the fluid into the compartment.

According to an embodiment of the device for microbial asexual reproduction-based fermentation, the blade disposed at a bottom of the transmission draft has a longest radius.

According to an embodiment of the device for microbial asexual reproduction-based fermentation, the second inlet of the refluxing tube is disposed higher than the blade disposed at the bottom of the transmission draft.

Accordingly, the present invention refluxes a solution into the tank together with a high pressure air to atomize the solution and increase oxygen content which is beneficial for microorganism reproduction.

In addition, the present invention can separate a cluster of the microorganism by the shear force generated from the plural silica sands for returning the microorganism to the logarithmic growth phase without sporulation, which achieves an efficacy of reducing fermentation time.

DETAILED DESCRIPTION OF THE PREFERRED EMBODIMENT

To provide a thorough understanding, the purpose and advantages of the present invention will be described in detail with reference to the accompanying drawings.

Figure 1:
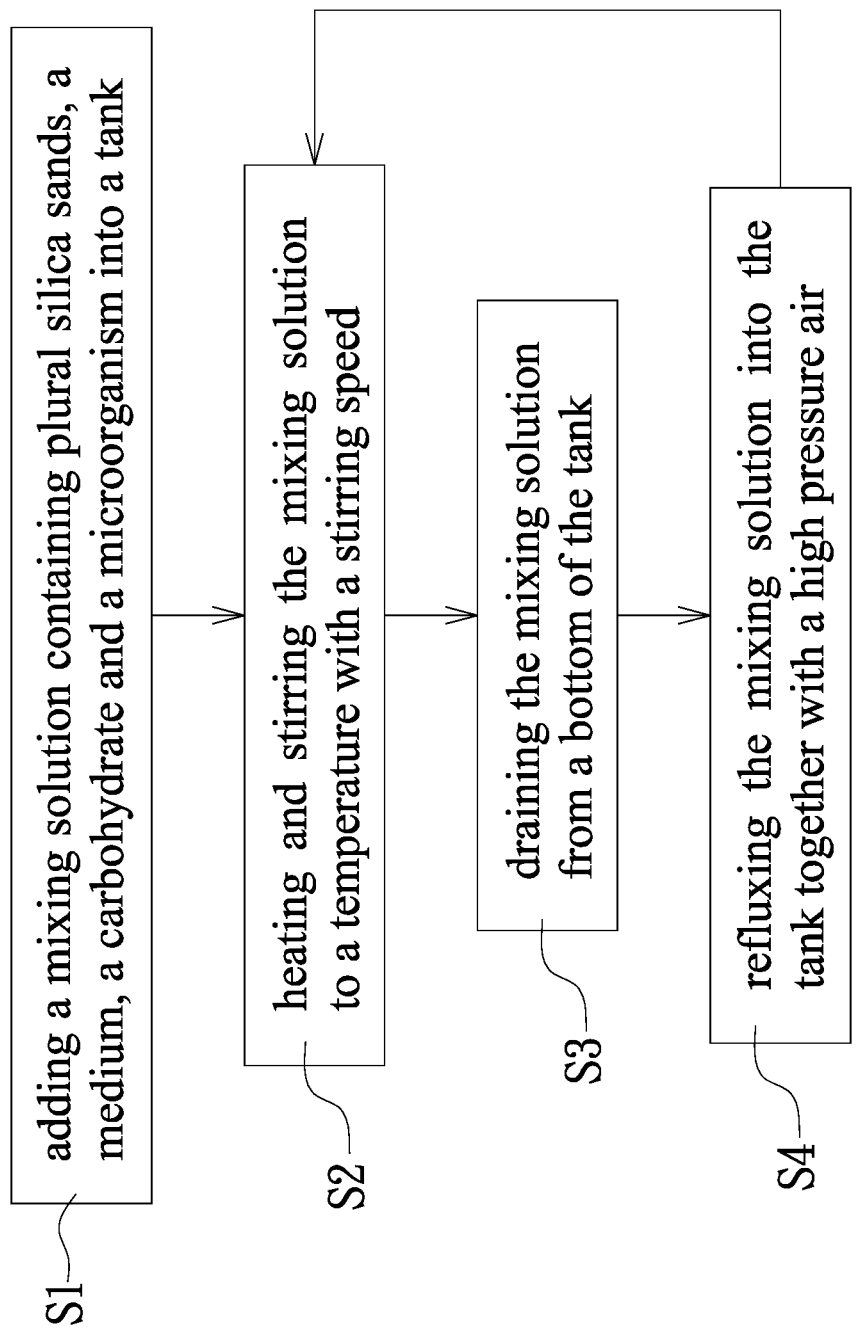
FIG. 1 is a flow chart showing a microbial asexual reproduction-based fermentation method of the present invention.
Figure 2:
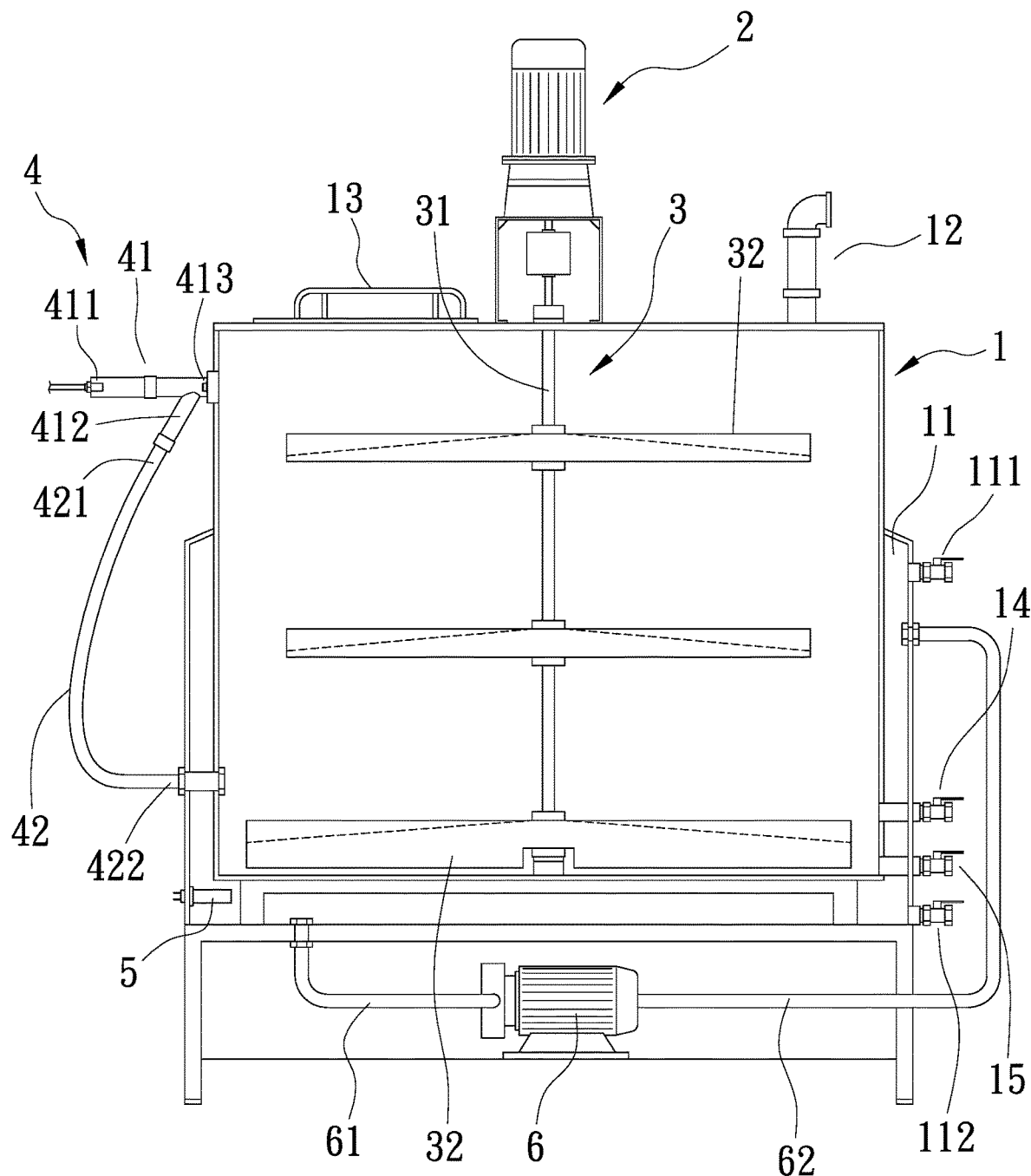
FIG. 2 is a schematic diagram showing a using device for microbial asexual reproduction fermentation of the present invention.

Referring to FIG. 1 and FIG. 2, a device for microbial asexual reproduction-based fermentation is disclosed, it comprises a tank (1), a speed control motor (2), a stirring component (3), a refluxing mechanism for high pressure air and water (4), a heating unit (5) and a pumping motor (6).

The tank (1) has a compartment (11), a ventilation valve (12), a feeding hole (13), an upper discharging opening (14) and a lower discharging opening (15). The compartment (11) is disposed around a lower region of a wall of the tank (1), and is provided with a first inlet (111) at an upper end and a first outlet (112) at a bottom end for injecting a fluid into or draining a fluid out of the compartment (11) respectively. The ventilation valve (12) is disposed at a top surface of the tank (1) for adjusting a pressure of the tank (1). The feeding hole (13) is used for importing a raw material into the tank (1), the upper discharging opening (14) is used for collecting a fermentation broth, and the lower discharging opening (15) is used for exporting plural silica sands, a medium and a microorganism.

The speed control motor (2) is disposed at a top side outside the tank (1) and having a power output terminal.

The stirring component (3) comprises a transmission shaft (31) and plural blades (32). The transmission shaft (31) is connected to the power output terminal of the speed control motor (2) and the plural blades (32) are disposed on the transmission shaft (31) at an interval in which the blade (32) disposed at a bottom of the transmission draft (31) has a longest radius.

The refluxing mechanism for high pressure air and water (4) comprises a Venturi tube (41) and a refluxing tube (42). The Venturi tube has a first input (411) for importing a high pressure air, a second input (412), and an output (413) connected to an upper side of the tank (1). The refluxing tube (42) has a second outlet (421) connecting to the second input (412) of the Venturi tube (41), and a second inlet (422) connecting to a lower side of the tank (1). A mixing solution in the tank (1) is drained from the tank (1) and injected to the second inlet (422) of the refluxing tube (42), and then exported to the second input (412) of the Venturi tube (41) from the second outlet (421) of the refluxing tube (42).

The heating unit (5) is disposed corresponding to the compartment (11) of the tank (1) for heating the solution in the compartment (11), and a content in the tank (1) is then heated indirectly.

The pumping motor (6) has a third inlet (61) and a third outlet (62). The third inlet (61) is connected to a lower side of the compartment (11) and the third outlet (62) is connected to an upper side of the compartment (11). After turning on the pumping motor (6), the fluid in the compartment (11) is pumped into the third inlet (61) and then re-injected into the compartment (11) from the third outlet (62) repeatedly to maintain a preset temperature of the fluid in the compartment (11).

Figure 3:
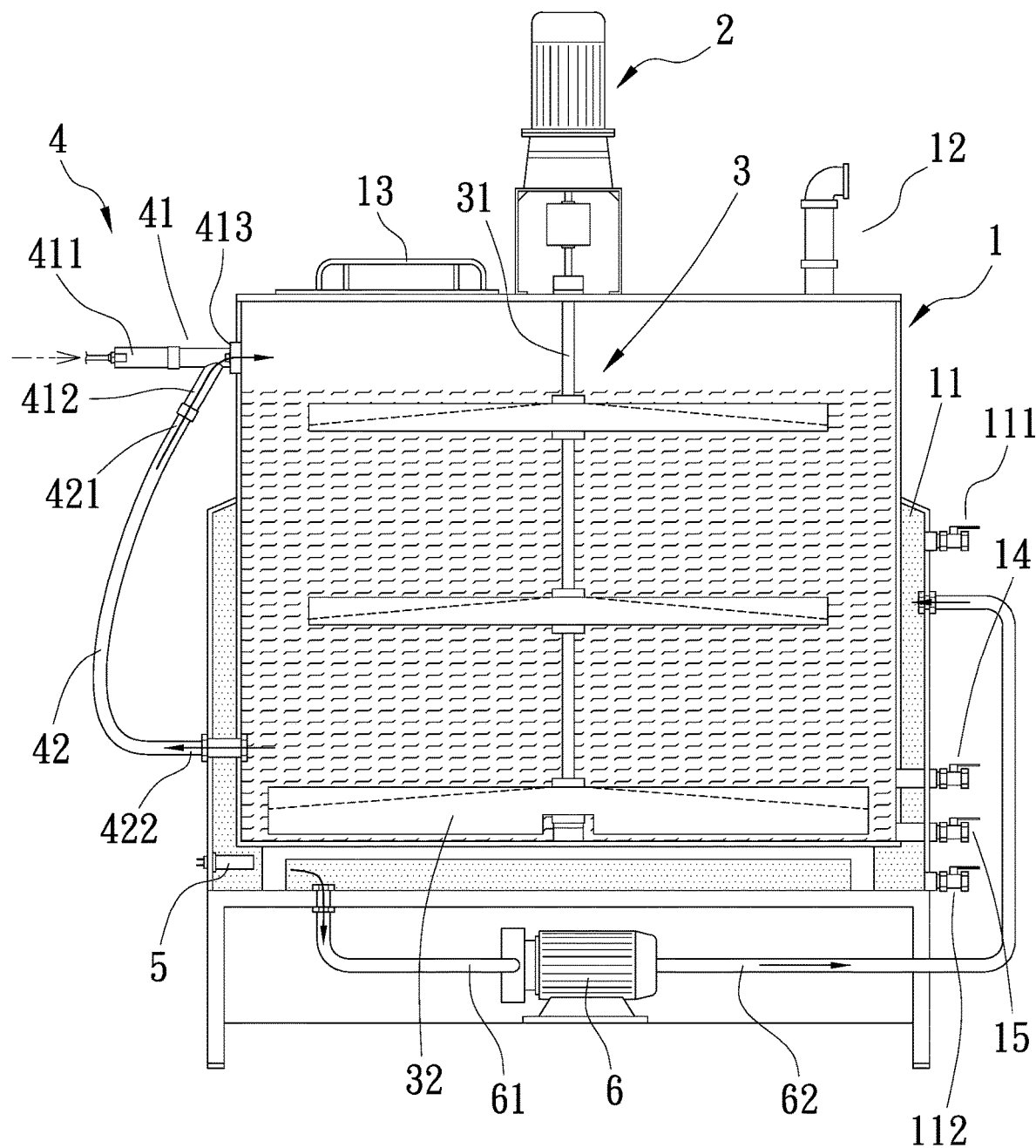
FIG. 3 is a schematic diagram showing a using device for microbial asexual reproduction fermentation in use of the present invention.
Figure 4:
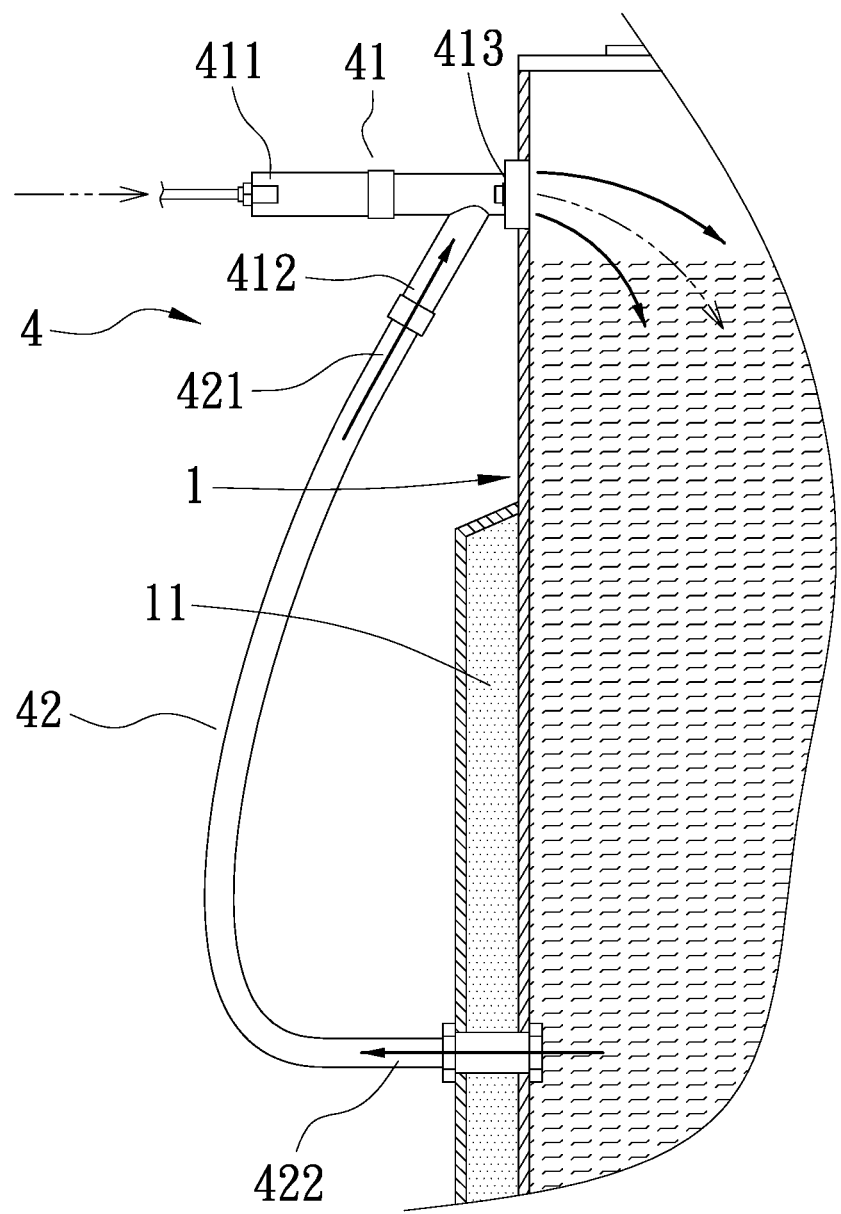
FIG. 4 is a partial enlarged diagram of FIG. 3.

Referring to FIG. 3 and FIG. 4, when conducting an microbial asexual reproduction-based fermentation by the device described above, plural silica sands, a medium, a carbohydrate and a microorganism are added into the tank (1) by the feeding hole (13), and a weight ratio of the plural silica sands, the medium and the carbohydrate is 1 wt %:3-5 wt %:3-24 wt %; then pure water is added into the tank (1) until the water horizontal line reaches a height equals to a height of the top blade (32) on the transmission shaft (31) for forming a mixing solution. The compartment (11) is also filled with water by the first inlet (111) and the heating unit (5) is turning on for heating the compartment (11) to heat the mixing solution in the tank (1) indirectly. When the temperature of the mixing solution reaches to a preset temperature, the speed control motor (2) is turned on for driving the transmission shaft (31) and the blades (32) of the stirring component (3) and stirring the mixing solution. The water in the compartment (11) is pumped into the third inlet (61) by the pumping motor (6) and re-injected into the compartment (11) from the third outlet (62) repeatedly to maintain a preset temperature of the water in the compartment (11). At the same time, the mixing solution at a bottom of the tank (1) is drained to the second inlet (422) of the refluxing tube (42) due to the Venturi effect, and flowed into the Venturi tube (41) from the second outlet (421) of the refluxing tube (42). A high pressure air is imported to the Venturi tube (41) of the refluxing mechanism for high pressure air and water (4) by the first input (411) to accelerated import the mixing solution in the Venturi tube (41) into the tank (1) by the output (413) of the Venturi tube (41), and the mixing solution refluxed is atomized instantly after entering the tank (1) and blended with oxygen for increasing oxygen content in water. Accordingly, interaction of the mixing solution having high-oxygen content and the microorganism accelerates reproduction rate of the microorganism. Furthermore, a strong shear force is generated from the plural silica sands by a stirring disturbance generated from the plural blades (32) which separates a cluster of the microorganism and returns the microorganism to a logarithmic growth phase without undergoing a spore phase to decrease a fermentation time of the microorganism.

Referring to FIG. 1 and FIG. 3, the method for fermentation based on microbial asexual reproduction by the device described above comprises:

Step 1 (S1): adding a mixing solution containing plural silica sands, a medium, a carbohydrate and a microorganism into a tank (1), and a weight ratio of the plural silica sands, the medium and the microorganism is 1 wt %:3-5 wt %:3-24 wt %;

Step 2 (S2): heating and stirring the mixing solution in the tank (1) to a temperature with a stirring speed for separating a cluster of the microorganism by a shear force generated from the plural silica sands and returning the microorganism to a logarithmic growth phase without undergoing a spore phase;

Step 3 (S3): draining the mixing solution from a bottom of the tank (1);

Step 4 (S4): refluxing the mixing solution into the tank (1) together with a high pressure air for atomizing and blending oxygen into the mixing solution when entering to the tank (1) and obtaining a small molecule water having a high level of oxygen to increase oxygen content in the environment for reproduction of an aerobic microorganism.

An embodiment is further disclosed below:

<Ingredient of the Mixing Solution>

Silica sands - - - 10 Kg

Soy powder - - - 30 Kg

Sucrose - - - 30 Kg

<<Fermentation Steps>>

1. 10 Kg of plural silica sands, 30 Kg of a soy powder and 30 Kg of sucrose were added into the tank (1); a pure water was added into the tank (1) until the water horizontal line reaches a height equals to a height of the top blade (32) on the transmission shaft (31), and the microorganisms were added into the tank (1) to obtain a mixing solution.

2. A clean water was added into the compartment (11) until the compartment (11) is fulfilling with 90% of clean water.

3. The heating unit (5) was turned on to heat the clean water in the compartment (11) and heat the mixing solution in the tank (1) indirectly to maintain a temperature of the mixing solution at 37° C.; the pumping motor (6) was also turned on to drain out the mixing solution from the tank (1), and the mixing solution was imported into the refluxing mechanism for high pressure air and water (4) and re-injected to the mixing solution into the tank (1).

4. The speed control motor (2) was turned on to drive the transmission shaft (31) and the blades (32) for stirring the mixing solution, the stirring speed of the speed control motor (3) is 300 rpm.

5. The microorganisms in the mixing solution were attached to the soy powder and formed plural clusters of the microorganism. The plural silica sands, the soy powder and the plural clusters of the microorganism are stirred by the plural blades (32) disposed on a lower region of the transmission shaft (31), and the clusters of the microorganism were separated by a shear force generated from the plural silica sands which returns the microorganism to a logarithmic growth phase without undergoing a spore phase to achieve an effect of rapid fermentation.

6. Simultaneously, a pure high pressure air is imported into the tank (1) by the Venturi tube (41) which pushes the mixing solution passing through the refluxing tube (42) and the Venturi tube (41) and re-injecting into the tank (1); the mixing solution was atomized by the pure high pressure air for blending with oxygen rapidly and the oxygen content of the mixing solution was increased up to 20 ppm; the oxygen in the mixing solution prevents reunion of water and provides a small molecule water having a high level of oxygen.

7. After fermentation and stopping stirring, the soy powder was precipitated at a bottom of the tank (1) since its density is higher than water, and most of derivatives of the microorganism were dissolved in the water phase and floated in an upper region of the mixing solution; so the fermentation broth is collected from the upper discharging opening (14), and the plural silica sands, the soy powder and the microorganism are collected from the lower discharging opening (15).

<Fermentation Broth Analysis>

When manufacturing liquor by traditional solid-state fermentation, it takes about a month to obtain an aged liquor; however, when manufacturing liquor by the present invention, it only takes 3 days to obtain the aged liquor with an alcohol by volume (ABV) of 14 degrees. The aged liquor obtained by the present invention can be further distilled to obtain a distilled liquor. ABV of the foreshot of the distilled liquor is 66 degrees, ABV of the heart of the distilled liquor is 45 degrees, and the aftershot of the distilled liquor is 35 degrees. In the present invention, distillation of a ton of the aged liquor can yield 120 L of the distilled liquor, and the average ABV of the distilled liquor is about 52 degrees. Content of unsaturated fatty acids in the distilled liquor obtained by the present invention is about 1900 ppm which is much higher than content of unsaturated fatty acids in a distilled liquor obtained from traditional solid-state fermentation. The unsaturated fatty acids in distilled liquor will transform into esters which is the source of wine flavor. Accordingly, the present invention can provide a liquor having better qualities than a liquor obtained by traditional solid-state fermentation.

The method of the present invention can also provide a microenvironment having high level of oxygen with a positive pressure state for the microorganism in the tank, and the microorganism in the tank will be not contaminated by the unwanted bacterial outside the tank. In addition, a high-oxygen environment can promote rapid reproduction of aerobic microorganisms, and the aerobic microorganisms having mitochondria can perform aerobic respiration and yield more ATP. Under the high-oxygen environment, ATP is easily transformed into saponin or terpenoid, so the fermentation broth obtained by the present invention can provide derivatives with higher value.

When supplementation of the high pressure air to the tank is stopped, the oxygen content of the mixing solution is decreased and an anaerobic condition is formed so as to control a reproduction status of aerobic microorganisms and anaerobic microorganisms.

What is claimed is:

1. A microbial asexual reproduction-based fermentation method, comprising:

adding a mixing solution containing plural silica sands, a medium, a carbohydrate, a microorganism and water into a tank;

heating the mixing solution to a temperature and stirring the mixing solution with a stirring speed in the tank, wherein the microorganism in said mixing solution forms a cluster of the microorganism attached to said medium, and where said plural silica sands, being exposed to the stirring at said stirring speed, generate a shear force sufficient for separating the cluster of the microorganism from said medium, and returning the microorganism to a logarithmic growth phase without undergoing a spore phase, thus reducing a fermentation time of the microorganism;

draining the mixing solution from a bottom of the tank; and refluxing the mixing solution drained from the bottom of the tank into the tank together with a high pressure air for atomizing the mixing solution and blending oxygen into the mixing solution to obtain water having a high level of oxygen and to increase oxygen content in said tank for reproduction of an aerobic microorganism.

2. The microbial asexual reproduction-based fermentation method as claimed in claim 1, wherein a weight ratio of the plural silica sands, the medium and the carbohydrate is 1:3-5:3-24.

3. The microbial asexual reproduction-based fermentation method as claimed in claim 2, wherein the medium is made of a soy powder.

4. The microbial asexual reproduction-based fermentation method as claimed in claim 3, wherein the carbohydrate is sucrose.

5. The microbial asexual reproduction-based fermentation method as claimed in claim 4, wherein the temperature is 37° C.

6. The microbial asexual reproduction fermentation method as claimed in claim 5, wherein the stirring speed is 300 rpm.

* * * * *